(12) United States Patent
Frisse et al.

(10) Patent No.: US 9,816,903 B2
(45) Date of Patent: Nov. 14, 2017

(54) FILTRATION DEVICE FOR LIQUID SAMPLES

(71) Applicant: SARTORIUS STEDIM BIOTECH GMBH, Göttingen (DE)

(72) Inventors: Andrea Frisse, Göttingen (DE); Andreas Graus, Nörten-Hardenberg (DE)

(73) Assignee: SARTORIUS STEDIM BIOTECH GMBH, Göttingen (DE)

( * ) Notice: Subject to any disclaimer, the term of this patent is extended or adjusted under 35 U.S.C. 154(b) by 0 days.

(21) Appl. No.: 15/119,677

(22) PCT Filed: Feb. 18, 2016

(86) PCT No.: PCT/EP2016/053426
§ 371 (c)(1),
(2) Date: Aug. 17, 2016

(87) PCT Pub. No.: WO2016/131904
PCT Pub. Date: Aug. 25, 2016

(65) Prior Publication Data
US 2016/0370267 A1 Dec. 22, 2016

(30) Foreign Application Priority Data
Feb. 19, 2015 (DE) .................. 10 2015 102 350

(51) Int. Cl.
*G01N 1/40* (2006.01)
*B01L 3/00* (2006.01)
*B01L 9/06* (2006.01)

(52) U.S. Cl.
CPC ............ *G01N 1/4077* (2013.01); *B01L 3/502* (2013.01); *B01L 9/06* (2013.01); *B01L 2200/025* (2013.01);
(Continued)

(58) Field of Classification Search
CPC .......... G01N 1/4077; G01N 2001/4088; B01L 3/502; B01L 9/06; B01L 2200/0689;
(Continued)

(56) References Cited

U.S. PATENT DOCUMENTS

| 2,952,255 A | 9/1960 | Hein, Jr. |
| 4,687,472 A | 8/1987 | Gross |

(Continued)

FOREIGN PATENT DOCUMENTS

| DE | 4432664 A1 | 3/1996 |
| DE | 69913978 T2 | 12/2004 |

(Continued)

OTHER PUBLICATIONS

International Search Report and Written Opinion issued on May 4, 2016 for application PCT/EP2016/053426, filed on Feb. 18, 2016 (Applicant—Satorius Stedim Biotech GmbH) (Original—12 pages) (German) // Translation of Written Opinion—2 pages).

(Continued)

*Primary Examiner* — Sally Merkling
(74) *Attorney, Agent, or Firm* — Ballard Spahr LLP

(57) ABSTRACT

Disclosed is a filtration device for liquid samples as well as a close and push-through device for said filtration device.

16 Claims, 5 Drawing Sheets

Figure 1:
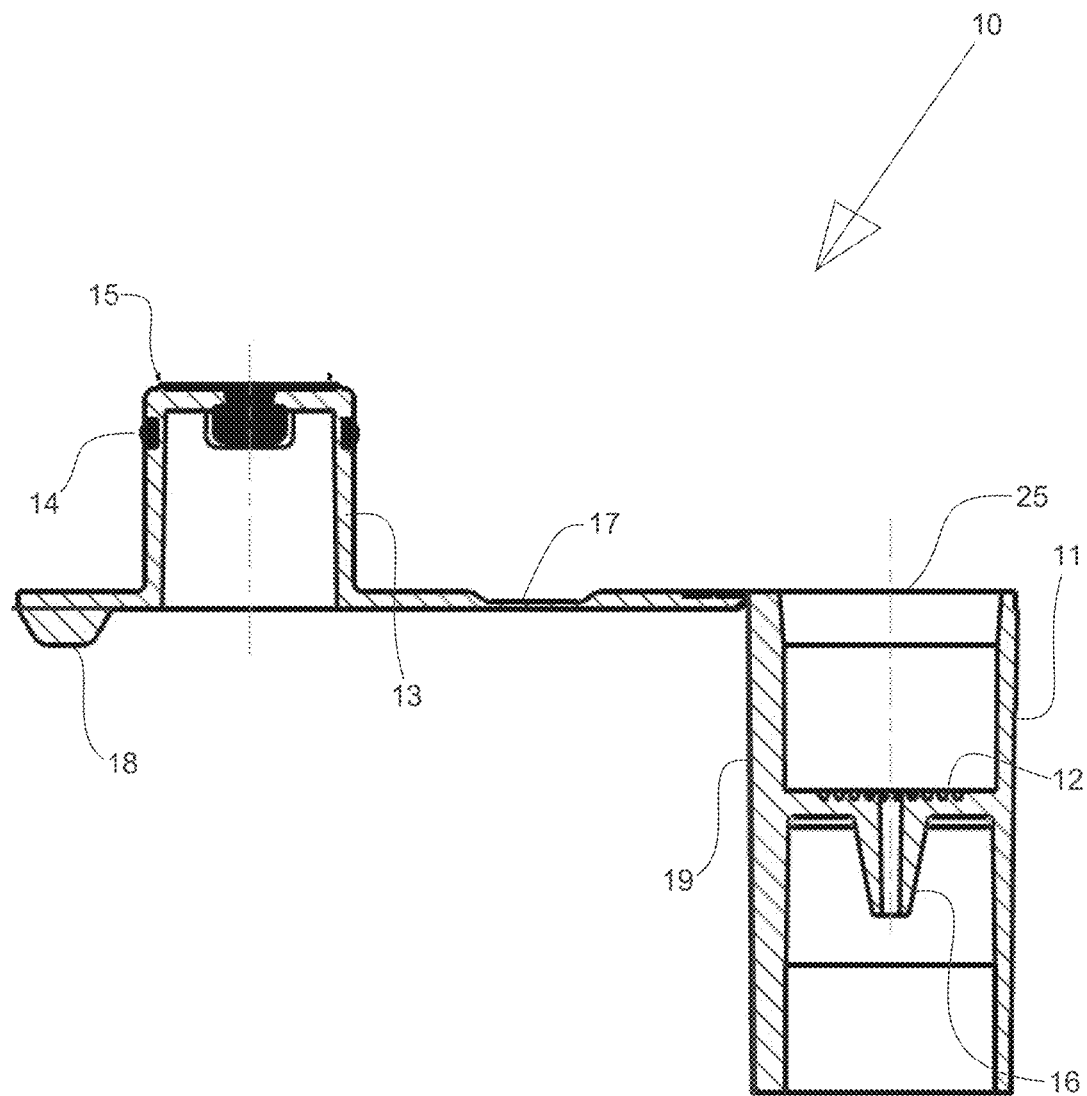

(52) U.S. Cl.
CPC . *B01L 2200/028* (2013.01); *B01L 2200/0689* (2013.01); *B01L 2300/043* (2013.01); *B01L 2300/0681* (2013.01); *B01L 2300/0832* (2013.01); *B01L 2300/12* (2013.01); *B01L 2400/0478* (2013.01); *G01N 2001/4088* (2013.01)

(58) Field of Classification Search
CPC ........... B01L 2200/025; B01L 2300/12; B01L 2400/0478; B01L 2200/028; B01L 2300/043; B01L 2300/0681; B01L 2300/0832
See application file for complete search history.

(56) References Cited

U.S. PATENT DOCUMENTS

| | | | | |
|---|---|---|---|---|
| 5,376,337 | A * | 12/1994 | Seymour | A61B 10/0051 422/401 |
| 7,306,740 | B2 * | 12/2007 | Freund | A61B 17/32002 210/781 |
| 7,387,216 | B1 * | 6/2008 | Smith | B01L 3/50825 215/DIG. 3 |
| 2008/0217264 | A1 * | 9/2008 | Leach | B01D 17/0217 210/787 |
| 2013/0270173 | A1 * | 10/2013 | Tortorella | B01L 3/502 210/416.1 |

FOREIGN PATENT DOCUMENTS

| | | |
|---|---|---|
| EP | 0297441 A2 | 1/1989 |
| EP | 0584714 | 3/1994 |
| JP | 34493 | 6/1919 |
| JP | H06-63134 A | 3/1994 |
| WO | WO-96/17084 A1 | 6/1996 |
| WO | WO-02/094343 A2 | 11/2002 |
| WO | WO-2005/055814 A2 | 6/2005 |
| WO | WO-2007/133615 A2 | 11/2007 |
| WO | WO-2009/055088 A1 | 4/2009 |
| WO | WO-2011/122841 A2 | 10/2011 |

OTHER PUBLICATIONS

GE Healthcare Life Sciences, "Speed up your (U)HPLC sample prep with Mini-UniPrep", Nov. 1, 2010, pp. 1-2, available at https://www.gelifesciences.com/gehcls_images/GELS/.

* cited by examiner

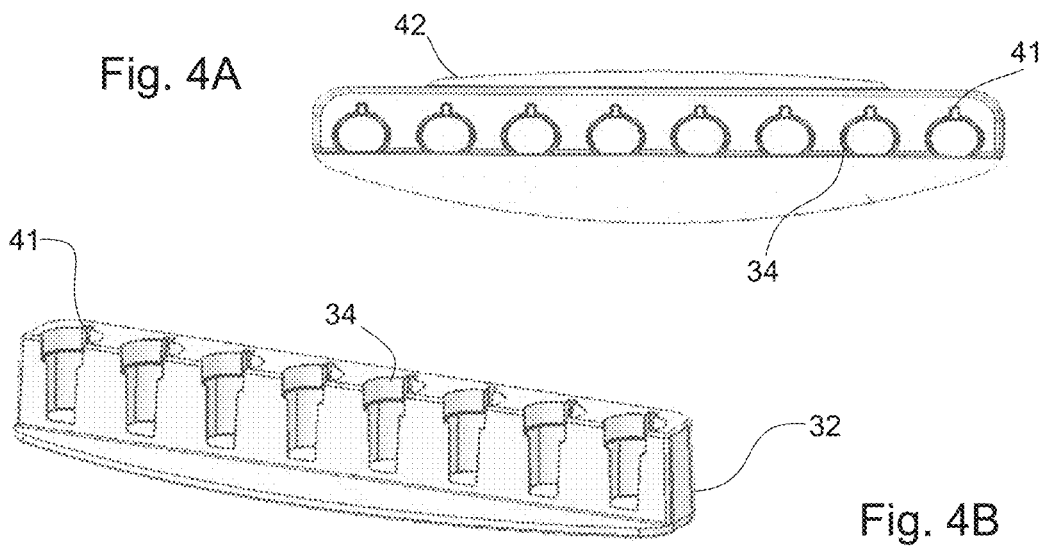
Fig. 4A
Fig. 4B
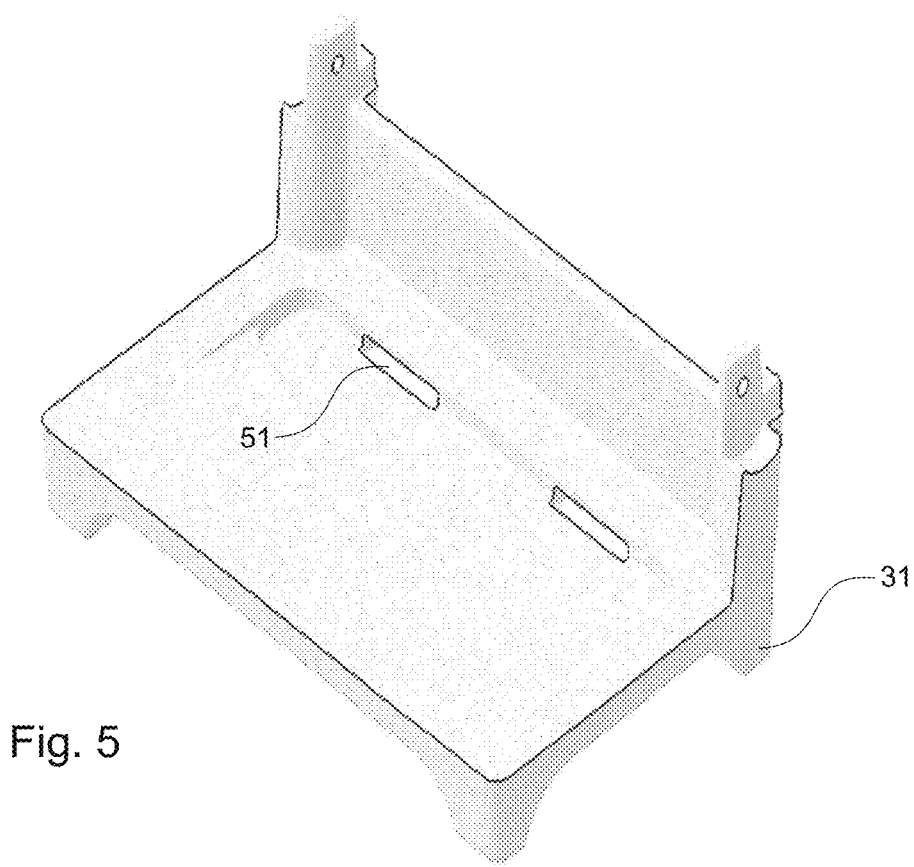
Fig. 5

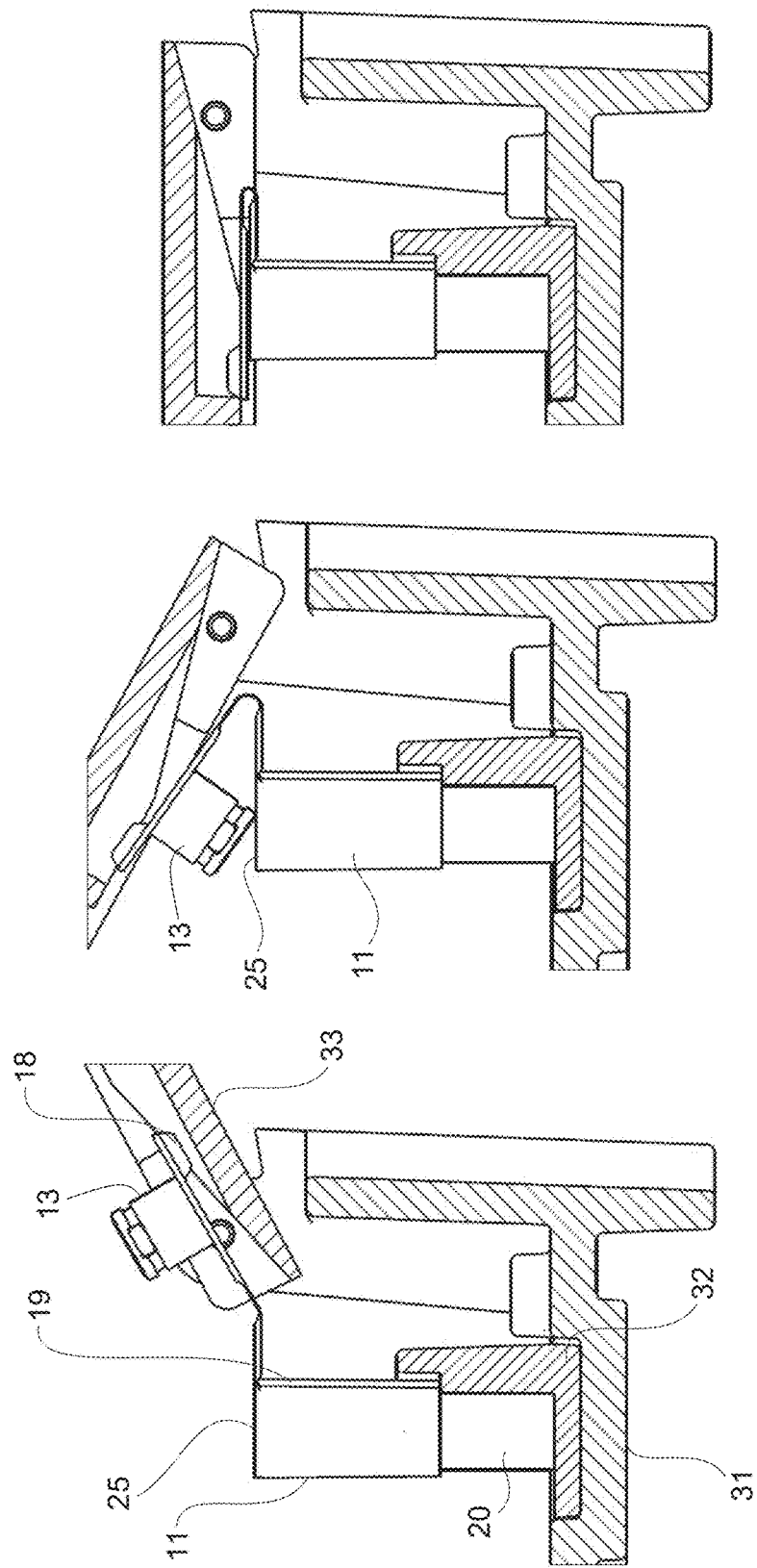

FILTRATION DEVICE FOR LIQUID SAMPLES

CROSS-REFERENCE TO RELATED APPLICATIONS

This application is a U.S. National Phase Application of International Application No. PCT/EP2016/053426, filed Feb. 18, 2016, which claims priority to German Patent Application No. 10 2015 102 350.4, filed Feb. 19, 2015, each of which are hereby incorporated by reference in their entirety.

The present invention relates to a filtration device for liquid samples according to the preamble of the independent claims.

Such filtration devices have been commercially available for quite some time. A system called Mini UniPrep® by the company GE/Whatman consists of a piston with a filter membrane, arranged at the bottom of the piston, and a collecting volume arranged thereabove. Said piston is configured to be form-locking to a sample vessel, and it is being inserted into the latter, which contains a liquid sample to be filtered, and is pressed down to the bottom of the sample vessel. Thereby the liquid sample to be filtered passes through the filter membrane, and the filtrate passes into the collection volume arranged thereabove. The particles that remain during filtration are being pressed through the filter membrane to the bottom of the sample vessel.

After filtration, the filtrate remains in the collection volume and is in permanent contact with the filter membrane. Thereby, matter can diffuse from the filter membrane into the sample liquid and thus contaminate the same.

An advancement of this product contains a collection vessel of glass within the piston, into which the filtrate is being brought from the collecting volume after filtration. In this way, a permanent contact of the filtrate and the filter membrane is prevented, and thus said contaminants are significantly reduced. However, manufacturing this product is very complex, the product consists of many parts and it bears the risk of glass breakage, since a large pressure has to be exerted upon pressing the piston into the sample vessel. It can therefore solely be used with matching push-through units, in order to protect the environment from broken glass, even if it is just a single sample that is being filtered.

Another system called Samplicity® by the company Millipore® consists of a vacuum device, into which one or more collecting vessels can be introduced. Subsequently, a membrane funnel is applied to each collecting vessel, the housing of the vacuum apparatus is closed and a vacuum is applied. In the process, the liquid sample is drawn through the filter of the membrane funnel, whereafter it dropwise enters into the collection vessel.

In addition to the high technical demands with regard to the vacuum device, this system also puts high technical demands on the membrane funnel used. Both the vacuum device and the membrane funnel are of high technical complexity. In addition, a negative pressure source is required, such as a vacuum pump.

It also turns out that applying negative pressure drives the filtration process less efficiently than excess pressure, as for example used in the UniPrep® system. This results in an overall longer filtration time.

Unlike a manual filtration process, with a system driven by a pump, dosing the filtration process is furthermore difficult, and operation noise arises that can be distracting.

It is therefore an object of the present invention to provide a device which avoids the disadvantages of the prior art. It is a further an object of the present invention to provide a filtration apparatus and a filtration method, which
(a) avoid contamination of the filtrate
(b) can be operated in a reliable and reproducible manner
(c) put low demands on equipment and technical peripherals
(d) allow a high throughput, and
(e) lead to low costs.

These and further objects are being solved by the methods and devices according to the independent claims of the present invention. The dependent claims describe preferred embodiments. Value ranges that are limited by numerical values in this document, always include the respective limits.

SUMMARY OF THE INVENTION

Before the invention is described in detail, it should be noted that this invention is not limited to certain parts of the devices described herein, or to steps of manufacture of the methods described herein, since these methods or devices may vary. It is also noted that the respective terminology is only for the purpose of certain described embodiments, and is not intentionally limited.

It should be noted that in the used description and in the appended claims, the simple form such as "a" or "the" includes the singular and/or the plural, except the context is clearly phrased differently. It is to be noted that in the event that a parameter range is specified, the limits belong to the disclosed or claimed range.

According to the invention, there is provided a filtration device for liquid samples comprising
a) a tube comprising an inlet end and an outlet end which define a longitudinal direction;
b) a filter surface arranged transversely to the longitudinal direction; and
c) a piston form-lockingly insertable into the tube from the inlet end, such that a liquid sample located above the filter surface within the tube is being pressed through the filter surface.

Introducing the piston into the tube causes an air cushion to be included as well, which is being compressed in the course of the process of insertion. This air cushion ensures on the one hand that there is only little contact between the liquid sample to be filtered and the piston, and on the other hand that the liquid sample is being entirely filtered through the filter surface. For very coarse filters the air cushion even gets pressed through the filter as well, and it also largely frees the filter of residual liquid, thereby improving the yield significantly.

The filtration device of the invention thus provides a solution for filtration that does not require the disposable syringes as conventionally used, and thus can be fed, for example, with a modern piston-operated pipette, such as of the brands Picus®, eLINE® or mLine® by Sartorius®. With an arrangement in a row, the filtration device can also be loaded with a multichannel pipette.

The filtration device of the invention is extremely easy to handle and typically consists of only a few individual components. It can be operated purely by means of physical strength, and renders an external source of power or impulsion, such as a vacuum pump, a pressure pump, or a centrifuge, dispensable.

Moreover, a method in which the liquid is pressed through a filter by means of pressure is faster than a method in which a liquid is drawn through a filter by means of negative pressure, as it generally takes longer until a sufficient vacuum has built up, whereas a positive pressure can be built up very quickly. Moreover, it is possible that the piston directly forces the fluid through the filter, and not by means of atmospheric overpressure.

The filtration device of the invention, moreover, has the advantage that the liquid sample to be filtered only briefly comes into contact with the filter surface, and in particular after the filtration process, contact between the filtrate and the filter surface is interrupted. In this way substances can be prevented from diffusing from the filter material into the sample liquid, and from thereby contaminating the same.

Once the filtration process is completed, the piston, which has been introduced into the tube, also serves as a lid.

Said samples may for example be samples for chemical or biological analysis or samples for chemical or biological processing. In such cases it is usually important to remove contaminants or foreign matter such as particles from the sample, in order not to impair subsequent analytical (HPLC, RCR, GC, MS, FPLC, sequencing) or preparative (recombinant biotechnology) steps.

In a particular embodiment the tube and/or the piston are made of a thermoplastic material selected from the group of polyethylene (PE) and high density polyethylene (HDPE), polypropylene (PP), polyvinyl chloride (PVC), polycarbonate (PC), copolyesters, acrylonitrile butadiene styrene (ABS), and styrene-acrylonitrile resin (SAN); an elastomer selected from the group of ethylene-propylene-diene monomer (EPDM) and liquid silicone rubber (LSR); a thermoplastic elastomer, preferably urethane-based thermoplastic elastomer, or a styrene block copolymer; a multicomponent plastic material selected from a mixture of polyethylene (PE) and polypropylene (PP), polypropylene (PP) and a thermoplastic elastomer, polycarbonate and a thermoplastic elastomer, and acrylonitrile butadiene styrene copolymer (ABS) and polypropylene (PP).

The choice of the plastic material depends in particular on the cost of the manufacturing process of the filtration device. In a specific embodiment, the device is intended to be a disposable article, so that for such applications, for reasons of costs, of their inert properties, of their mechanical strength and of their temperature resistance, the well-known injection moldable thermoplastic materials polyethylene, polypropylene, polyvinylidene fluoride, or polyether ether ketone can be used. High density polyethylene, which has a high resistance to chemicals, mechanical stress and extreme temperatures, can also be used.

In addition, the tube and/or the piston are preferably made of a transparent material to allow an insight into the filtration process.

Preferably the filter surface is configured to act as a support for a filter matrix.

Preferably a material is used as the a material for the filter matrix selected from the group that includes PTFE, polyethersulfone, paper, regenerated cellulose, nitrocellulose, glass fiber, nylon, and/or cellulose acetate. Preferably the filter matrix is designed in the form of a membrane. Preferably the filter matrix has a mean pore size from ≤100 microns to ≥0.01 microns. Particularly preferred comprises from ≤10 microns to ≤0.1 microns. Most preferably, the filter matrix has a mean pore size from ≤0.45 microns to ≥0.2 microns.

Preferably the filter matrix is placed in a support carrier, in which the filter matrix is seated on a filter surface or is fixed thereon, and is equipped, from above, with a continuous spacer with respect to the piston that is pressed down, with the spacer extending over the entire surface of the filter matrix.

It is preferred that the fixing is carried out in such a way that towards the inlet end no dead space forms between the filter matrix and the piston, which is completely inserted into the tube.

This is for example accomplished by not providing any clamping ring in the direction of the inlet end that holds the filter matrix on the filter surface.

This can preferably be achieved by heat sealing, ultrasound, adhesion, or by clamping. Thus for example in thermal fixing, the filter membrane adheres onto the filter surface, which e.g. consists of polypropylene (PP), without any dead space being generated towards the inlet end between the filter membrane and the piston, which is completely inserted into the tube.

In a preferred embodiment the piston includes a circumferential elevation at an edge of the end that faces the filter surface.

This circumferential elevation prevents the filter matrix from being harmed when the piston is inserted into the tube, for example by particles present between the piston and the filter matrix or by an unevenness of the filter surface. Furthermore, adhesion of the filter matrix to the piston is being prevented. If applicable, in this case, a minimal dead volume generated by the circumferential elevation is acceptable.

The circumferential elevation may press the filter matrix peripherally to the filter support. Preferably the circumferential elevation is designed in such a way that it engages a correspondingly shaped notch in the filter surface or a peripheral edge surrounding the filtering surface, when the piston is being inserted into the tube. Thereby any dead volume is minimized that could form between the filter surface or the filter matrix and the piston.

Preferably the filter surface furthermore contains a drip director, oriented toward the outlet end of the tube.

Said drip director may, for example, be shaped as a funnel, arranged below the filter surface, which directs the liquid flow that passes the filter area, on target into a collecting vessel arranged underneath the same.

Preferably the piston is connected to the tube via a hinge.

Such a hinge is preferably a film hinge. In such an embodiment, the combination of the tube and the piston is preferably formed in one piece, for example by means of injection molding.

In a further preferred embodiment the piston comprises
  (a) a circumferential bead or
  (b) a circumferential notch for a sealing ring.

The circumferential bead can be an integral part of the piston material and may, for example, have been directly formed during injection molding of the piston.

Alternatively, the circumferential bead may have been integrally shaped onto the piston by means of a two-component process, for example by gating. In this respect it is preferred to use a material with better sealing properties (softer and more resilient, respectively). In this way, the piston can be rendered more smooth-running and the seal can also be improved.

Alternatively, the piston may also be configured without a circumferential bead or seal ring. In this case, the sealing effect is achieved by a sufficiently tight fit between the piston and the tube.

In a further embodiment the filtration device includes
  (a) a guide arranged at the outer wall of the tube, and/or
  (b) a guide that is arranged at the side of the piston facing the inlet end.

Said guide arranged at the outer wall of the tube can for example be arranged at the outer wall of the tube in the longitudinal direction, for example in the form of a guide web which engages in a corresponding notch in a positioning site for a collecting vessel with a filtration device arranged thereon, thus allowing the filtration device to be orientated a reproducible manner.

Said guide may also be designed as a notch, which engages in a corresponding guide web at the positioning site.

Said guide arranged on the side of the piston that is oriented in the same direction as the inlet end—i.e. at the "top side" of the piston—may for example be designed in the form of a web, which engages in a corresponding notch in a close and push-through device, upon actuation of which the piston is inserted into the tube by means of a reproducible movement, such that a liquid sample present above the filter surface in the tube is being pressed through the filter surface.

Said guide may also be designed as a notch that engages with a corresponding web at the close and push-through device.

According to the invention there is furthermore provided a kit, consisting of a filtration device according to one of the preceding claims and a collection vessel.

Said collecting vessel preferably includes a material selected from the group containing glass, polypropylene, or another suitable material. Preferably, clear or brown glass vials, optionally with additional vial inserts for small sample volumes, may be used.

Preferably the collecting vessel has a volume in the range between ≥0.05 and ≤2 ml. Commercially available collecting vessels, such as for instance those used for HPLC, are e.g. available in the size 12×32 mm.

In one embodiment of this kit, the collecting vessel may also be an integral part of the filtration device. In this case, moreover, a predetermined breaking point between the collecting vessel and the filtration device may be provided, by means of which the latter can be removed after the filtration process, so that the collecting vessel can then be used in subsequent process steps.

Preferably the collecting vessel includes an external diameter that is less than the inner diameter of the outlet end of the tube of the filtration device of the invention. In this way the latter may be positioned on the collecting vessel prior to the filtration process. Preferably the tube is pulled over the collection vessel up to the bottom of the filter surface. Thereby a kit consisting of the filtration device and a collecting vessel is provided with additional stability, since the filtration unit seated on the collecting vessel cannot fall off or be pushed off the collecting vessel sideways.

According to the invention there is furthermore provided a close and push-through device for a filtration device according to any of the preceding claims, comprising
 a base.
 at least one positioning site for a collecting vessel, arranged at the base, as well as
 a lid hinged to the base,
 wherein the lid is configured in such a way that during a closing movement of the lid about the hinge axis towards the base
  a piston of a filtration device is being introduced into the tube of a filtration device wherein the filtration device is arranged on a collecting vessel which is present in the positioning site.

Said at least one positioning site for a collecting vessel may be designed as a vertical recess in the base, into which the collecting vessel can be positioned.

It is particularly preferred for said close and push-through device that (a) the positioning site for at least one collecting vessel contains a guide for the filtration device or the tube thereof, and/or
(b) the lid contains a guide for the piston of at least one filtration device.

Said guide at the positioning site for a collecting vessel can for example be configured in the form of a notch or a web, which engages a corresponding web or notch, respectively, at the outer wall of the tube of the filtration device.

Said guide at the lid may for example be configured in the form of a notch or a web that engages in a corresponding web or notch, respectively, on the side of the piston of the filtration device oriented in the same direction as the inlet end.

The interplay of (i) the guide at the positioning site for a collecting vessel and (ii) the guide at the outer wall of the tube of the filtration device permits an ever-reproducible orientation of the filtration device. The interaction of the guides at (i) the lid of the close and push-through device and (ii) at the side of the piston of the filtration device that is oriented in the same direction as the inlet end, permits an automated and ever-reproducible close and push-through process.

It is a prerequisite for the latter that the filtration device is oriented in a reproducible manner in the positioning site. Furthermore, said close and push-through process is facilitated if the piston is connected to the tube of the filtration device by a hinge, preferably by a film hinge.

Hence, in this embodiment simultaneous filtration of a plurality of samples by means of manual operation can be carried out in a fast, safe and reproducible manner.

Preferably the positioning site for a collection vessel is configured to be removable from the base.

In this way several collecting vessels may for example be arranged in the positioning site outside the close and push-through device, the filtration devices may be arranged on the collecting vessels, and/or the liquid samples may be introduced into the filtration devices.

In this embodiment operating multichannel pipettes is for example considerably facilitated. The positioning site may be configured in such a way that it predefines a distance measure between individual collecting vessels that corresponds to the distance measure of multichannel pipettes.

Subsequently the positioning site is positioned within the base, and the lid of the close and push-through device is being closed. In the process the pistons of the filtration devices are inserted into the tubes of the latter and the samples are pressed through the filter surface.

The latter process is simplified and automated by the guides that are optionally arranged at the outer walls of the tubes and at the pistons of filtration devices and positioning sites, respectively, and at the lids of the close and push-through device.

Preferably the removable positioning site contains a recess or protrusion, which engages in a complementary protrusion or recess at the base when introduced into the base, to prevent tipping of the positioning site.

Such protrusion at the positioning site may for example be a web, a lip or one or more pins or dowels, which engage(s) in (a) corresponding recess(es) at the base.

Such a recess at the base may for example include a notch, a web, or a bore that engages a corresponding protrusion at the base.

DRAWINGS AND EXAMPLES

The present invention is explained in more detail by means of the figures and examples shown and discussed in the following. It is to be noted that the figures and examples are only descriptive and are not intended to limit the invention in any way.

FIG. 1 shows a filtration device 10 of the invention for liquid samples, comprising a tube 11 comprising an inlet end and an outlet end, which define a longitudinal direction, as well as a filter surface 12, arranged transversely to the longitudinal direction, as well as a piston 13, which is insertable into the tube 11 in a form-fitting manner from the inlet end, such that a liquid sample located above the filter surface within the tube is being pressed through the filter surface.

The filter surface 12 serves as a support for a filter matrix, which is not shown in FIG. 1.

To seal against the inner wall of the tube 11, the piston 13 contains a circumferential bead 14, which is for example integrally shaped on the piston by a two-component process. In this process, material with suitable sealing properties (softer and more resilient, respectively) is used. In this way, the piston can be rendered smoother and the seal can also be improved.

The piston 13 furthermore contains a circumferential elevation 15 at an edge of its side facing the filter surface 12, which is shown in exaggerated height in FIG. 1. This circumferential elevation prevents the filter matrix from being harmed upon insertion of the piston 13 into the tube 11, for example by particles located between the piston and filter matrix or by unevenness of the filter surface 12. Furthermore, adhesion of the filter matrix to the piston is being prevented.

The filter surface 2 includes a drip director 16 facing the outlet end of the tube.

The piston 13 is connected to the tube 11 by a film hinge 17. The combination of the tube 11 and the piston 13 may be integrally formed, for example by means of an injection molding process.

Furthermore, a guide 18 arranged on the side of the piston oriented in the same direction as the inlet end, and a guide 19 arranged at the outer wall of the tube 11 are visible.

The first guide is designed in the form of a web, which engages a corresponding notch in a close and push-through device, which is inserted into the tube during actuation of the piston by means of a reproducible movement, such that a liquid sample located above the filter surface in the tube is being pressed through the filter surface.

The latter guide is designed in the form of a web, which engages a corresponding notch in a positioning site for a collecting vessel with a filtration device arranged thereon, thus permitting a reproducible orientation of the filtration device.

Figure 2A:
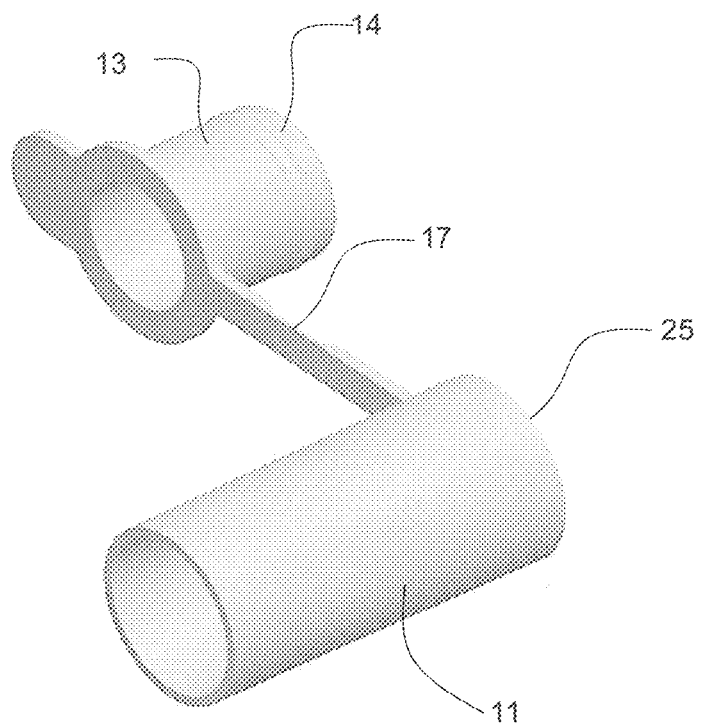
Figure 2B:
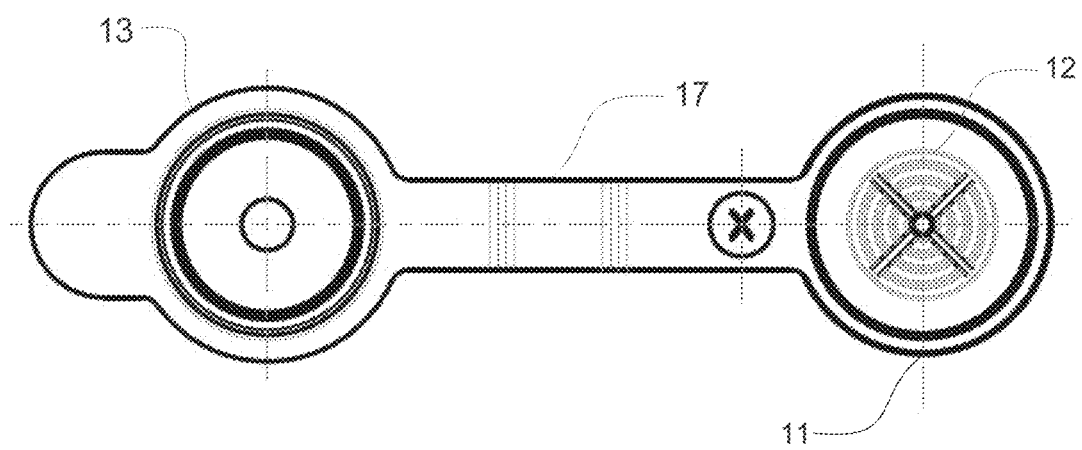

FIG. 2 depicts a filtration device of the invention that includes a tube 11 and a piston 13 in an oblique (FIG. 2A) and plan view (FIG. 2B). The guides discussed above are not shown in FIG. 2.

Figure 3:
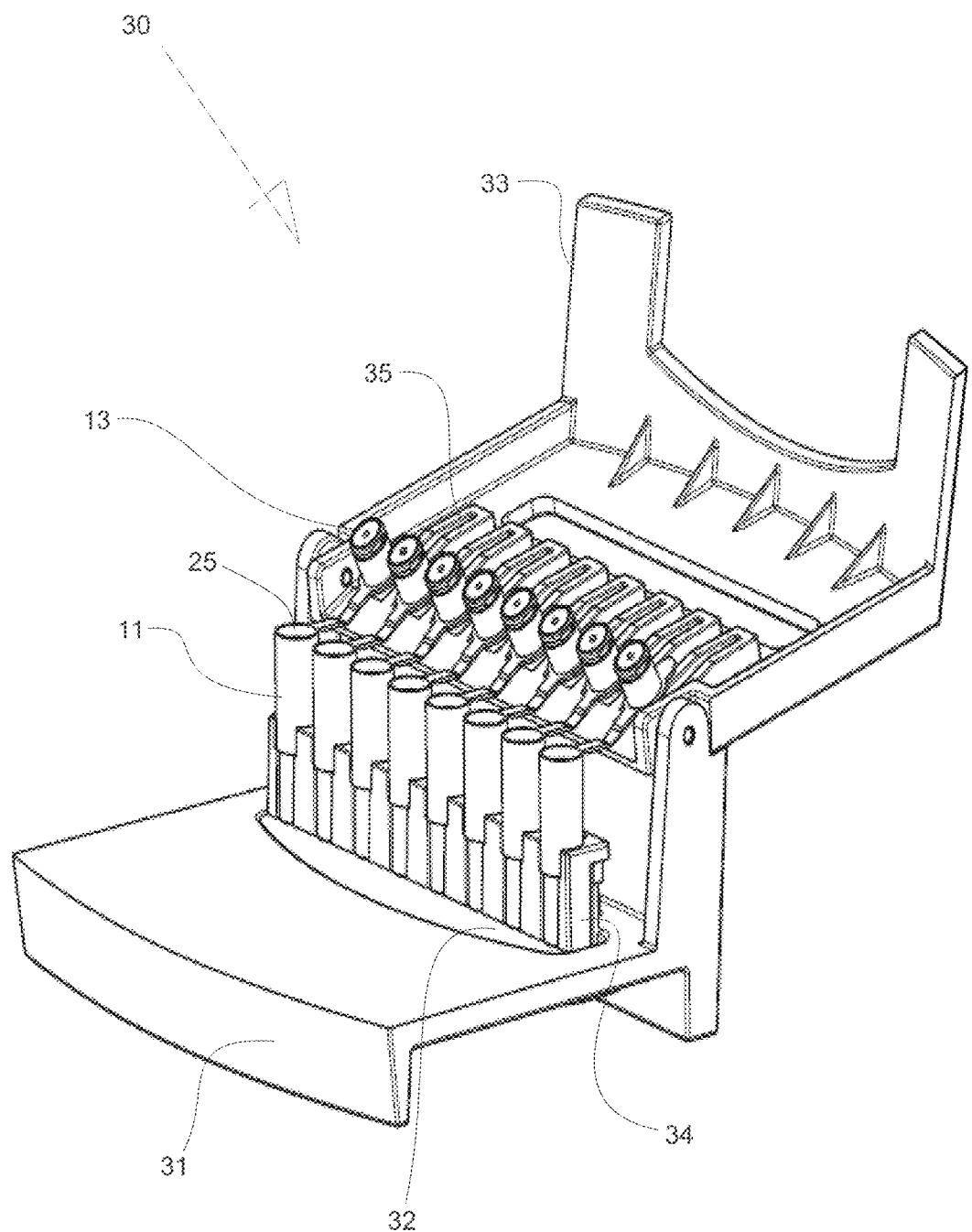

FIG. 3 depicts a close and push-through device 30 for the filtration device described above, which includes a base 31, a positioning site 32 for collecting vessels arranged at the base, as well as a lid 33 hinged to the base.

The lid 33 is configured in such a way that, during a closing movement of the lid 33 about the hinge axis towards the base 31, a piston 13 of a filtration device is introduced into the tube 11 of the filtration device.

Said filtration device is arranged on a collecting vessel present in the positioning site.

The lid 33 of the close and push-through device 30 further includes guides 35 for the pistons 13 of the filtration devices. These guides are designed in the form of a notch, into which corresponding webs engage, which are arranged on the side of the piston 13 that faces the inlet end.

FIG. 4 depicts the positioning site 32 for collecting vessels in a configuration that is removable from the base 31. The positioning site 32 includes guides 34 for the filtration devices 10 that contain a notch 41, into which corresponding webs on the outer wall of the tube engage.

To prevent tipping of the positioning site, the removable positioning site 32 further includes a protrusion 42, which engages in a complementary recess at the base when being positioned in the base 31.

FIG. 5 depicts the base 31 of the close and push-through device that includes recesses 51, into which engage the above discussed protrusions on the positioning site.

FIG. 6 depicts the filtration process in a close and push-through device 30 of the invention in three partial steps. Positioning sites 32 are arranged in a base 31, and in the positioning sites there are arranged collecting vessels. Above the collecting vessels, there are arranged the filtration devices, comprising a tube 11, a filter surface, not shown, and a piston 13, which is form-fittingly insertable into the tube 11. The close and push-through device further comprises a lid 33 hinged to the base 31.

Furthermore, a guide 18 arranged at the side of the piston 11 that is oriented in the same direction as the inlet, and a guide 19 arranged on the outer wall of the tube 11 can be seen.

The guide 18 is designed in the form of a web, which engages a corresponding notch in the lid 33 of the close and push-through device. As shown in FIGS. 6B and 6C, when the lid is actuated, the piston is inserted into the tube 11 by means of a reproducible movement, such that a liquid sample located above the filter surface in the tube is being pressed through the filter surface.

The guide 19 is designed in the form of a web, which engages a corresponding notch 41 in the positioning site 32 for a collection vessel on which there is arranged a filtration device, and the guide thus permits a reproducible orientation of the filtration device in the positioning site.

The invention claimed is:

1. A filtration device (10) for liquid samples, comprising
   a) a tube (11) comprising an inlet end and an outlet end, which define a longitudinal direction,
   b) a filter assembly (12) arranged transversely to the longitudinal direction and positioned within the tube between the inlet and outlet ends of the tube, the filter assembly having a first surface facing the inlet end of the tube and an opposing second surface facing the outlet end of the tube, and
   a piston (13) movably connected to the tube and form-lockingly insertable into the tube from the inlet end,
      wherein the piston is selectively moveable to a closed position in which the piston is at least partially received within the inlet end of the tube and at least partially advanced in the longitudinal direction toward the filter assembly, and wherein the filter assembly is configured to permit flow of liquid through the filter assembly from the first surface of the filter assembly to the opposing second surface of the filter assembly, such that a liquid sample located above the filter assembly within the tube is pressed through the filter assembly by advancement of the piston within the tube.

2. The filtration device according to claim 1, wherein at least one of the tube and the piston is made of a material selected from the group comprising polyethylene, polypropylene, polyvinylidene fluoride, polyether ether ketone, and/or high density polyethylene.

3. The filtration device according to claim 1, further comprising a filter matrix, wherein the first surface of the filter assembly acts as a support for the filter matrix.

4. The filtration device according to claim 3, wherein the filter matrix is fixed onto the first surface of the filter assembly.

5. The filtration device according to claim 1, wherein the piston comprises:
    an end facing the first surface of the filter assembly; and
    a circumferential elevation (15) at an edge of the end facing the first surface of the filter assembly.

6. The filtration device according to claim 1, wherein the filter assembly comprises a drip director (16) facing the outlet end of the tube and extending from the first surface of the filter assembly to the second surface of the filter assembly.

7. The filtration device according to claim 1, wherein the piston comprises
    a) a circumferential bead or
    b) a circumferential notch for a sealing ring (14)
for sealing against an inner wall of the tube.

8. The filtration device according to claim 1, wherein filtration device comprises
    a) a guide (19) arranged at an outer wall of the tube (11), or
    b) a guide (18) arranged at an end of the piston oriented in the same direction as the inlet end of the tube.

9. A kit consisting of a filtration device according to claim 1 and a collection vessel.

10. A close and push-through device (30) for a filtration device according to claim 1, comprising
    a base (31)
    at least one positioning site (32) for a collecting vessel at the base (31), and
    a lid (33) hinged to the base and configured for movement about a hinge axis,
    wherein the lid is configured to introduce a piston of a filtration device into the tube of the filtration device during a closing movement of the lid about the hinge axis toward the base, and
    wherein said filtration device is arranged on a collecting vessel in the positioning site,
    wherein the collecting vessel is positioned in fluid communication with the outlet end of the tube of the filtration device.

11. The close and push-through device according to claim 10, wherein
    a) the positioning site (32) for a collecting vessel comprises a guide for a filtration device or the tube thereof, or
    b) the lid comprises a guide for the piston of at least one filtration device.

12. The close and push-through device according to claim 10, wherein the positioning site for a collecting vessel is removable from the base.

13. The close and push-through device according to claim 12, wherein the removable positioning site comprises a recess or protrusion (42), which when being introduced into the base, engages a complementary protrusion or recess (51), respectively, at the base, to prevent tipping of the positioning site.

14. The filtration device according to claim 1, wherein the filtration device comprises a guide (19) arranged at an outer wall of the tube (11), and a guide (18) arranged at an end of the piston oriented in the same direction as the inlet end.

15. The close and push-through device according to claim 10, wherein the positioning site (32) for a collecting vessel comprises a guide for a filtration device or the tube thereof, and the lid comprises a guide for the piston of at least one filtration device.

16. The filtration device according to claim 1, wherein the piston is movably connected to the tube by a film hinge.

* * * * *